United States Patent [19]
Suprise et al.

[11] Patent Number: 6,142,983
[45] Date of Patent: *Nov. 7, 2000

[54] DISPOSABLE ABSORBENT ARTICLE HAVING AN ABSORBENT SUPPORT SYSTEM

[75] Inventors: Jody Dorothy Suprise, Pine River; Barbara Ann Owen, Menasha, both of Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/938,429

[22] Filed: Sep. 26, 1997

[51] Int. Cl.$^7$ ...................................................... A61F 13/15
[52] U.S. Cl. ................................ 604/385.03; 604/385.21; 604/385.23; 604/385.26; 604/385.28; 604/386; 604/391; 604/392; 604/398
[58] Field of Search .................................. 604/385.1–386, 604/391–402, 385.01–385.03, 385.21–385.31; 602/70

[56] References Cited

U.S. PATENT DOCUMENTS

| | | | |
|---|---|---|---|
| 1,201,860 | 10/1916 | Nelke . | |
| 2,028,602 | 1/1936 | Hanson | 2/70 |
| 2,052,598 | 9/1936 | Berg | 604/395 |
| 2,636,494 | 4/1953 | Hon | 604/398 |

(List continued on next page.)

FOREIGN PATENT DOCUMENTS

| | | |
|---|---|---|
| 0 217 032 | 4/1987 | European Pat. Off. . |
| 0 382 022 | 8/1990 | European Pat. Off. . |
| 94/10389 | 12/1994 | South Africa . |
| 10273 | 4/1897 | United Kingdom ................... 604/401 |
| 0 620 555 | 1/1947 | United Kingdom . |
| 0 636 684 | 3/1947 | United Kingdom . |
| 2 112 268 | 7/1983 | United Kingdom . |
| 2 273 646 | 6/1994 | United Kingdom . |
| 91/08725 | 6/1991 | WIPO . |
| 92/05089 | 4/1992 | WIPO . |
| 92/12648 | 8/1992 | WIPO . |
| 95/22306 | 8/1995 | WIPO . |
| 96/03950 | 2/1996 | WIPO . |

*Primary Examiner*—John G. Weiss
*Assistant Examiner*—K. M. Reichle
*Attorney, Agent, or Firm*—Jeffrey B. Curtin

[57] ABSTRACT

A disposable absorbent article defines an outer cover, an absorbent chassis and an absorbent support member which is configured to maintain the absorbent chassis close to a wearer's body in use. The absorbent chassis includes a backsheet, a bodyside liner which is connected to the backsheet in a superposed relation and an absorbent core disposed between the backsheet and the bodyside liner. The absorbent chassis is attached to the outer cover at the waist edges and remains at least partially unattached from the outer cover between the waist edges. The absorbent support member is attached to the absorbent chassis and extends between and connects the absorbent chassis to the side edges of the outer cover. The absorbent support member maintains the absorbent chassis in a close, conforming fit with the wearer's body even after the chassis becomes saturated with body exudates while the outer cover is free to move independently from the absorbent chassis. Thus, the disposable absorbent article has an aesthetically pleasing garment-like appearance and has improved fit and containment during use.

37 Claims, 3 Drawing Sheets

U.S. PATENT DOCUMENTS

| | | |
|---|---|---|
| 2,839,057 | 6/1958 | Argyll . |
| 2,863,455 | 12/1958 | Holce ................................................ 604/395 |
| 3,162,196 | 12/1964 | Salk .................................................. 604/399 |
| 3,368,562 | 2/1968 | Vogt . |
| 3,592,194 | 7/1971 | Duncan . |
| 3,608,551 | 9/1971 | Seijo ................................................. 604/397 |
| 3,687,141 | 8/1972 | Matsuda ............................................ 604/397 |
| 3,727,238 | 4/1973 | Wolfson ................................................ 2/69 |
| 3,954,107 | 5/1976 | Chesky et al. . |
| 4,247,959 | 2/1981 | Rose .................................................... 2/212 |
| 4,280,230 | 7/1981 | LaFleur ................................................ 2/408 |
| 4,327,448 | 5/1982 | Lunt .................................................... 2/404 |
| 4,459,705 | 7/1984 | Langford ............................................. 2/105 |
| 4,475,912 | 10/1984 | Coates . |
| 4,488,317 | 12/1984 | Polsky ................................................. 2/227 |
| 4,555,245 | 11/1985 | Armbruster ...................................... 604/396 |
| 4,631,062 | 12/1986 | Lassen et al. . |
| 4,663,220 | 5/1987 | Wisneski et al. ................................. 428/221 |
| 4,704,116 | 11/1987 | Enloe . |
| 4,745,636 | 5/1988 | Lunt .................................................... 2/402 |
| 4,747,846 | 5/1988 | Boland et al. . |
| 4,797,955 | 1/1989 | Garrett ................................................ 2/213 |
| 4,808,177 | 2/1989 | Des Marais et al. ........................ 604/385.1 |
| 4,834,738 | 5/1989 | Kielpikowski et al. ..................... 604/385.2 |
| 4,846,825 | 7/1989 | Enloe et al. ................................ 604/385.2 |
| 4,872,871 | 10/1989 | Proxmire et al. .............................. 604/394 |
| 4,892,598 | 1/1990 | Stevens ............................................ 604/399 |
| 4,935,021 | 6/1990 | Huffman et al. ............................ 604/385.1 |
| 5,052,058 | 10/1991 | Mueller ................................................ 2/228 |
| 5,226,992 | 7/1993 | Morman .............................................. 156/62.4 |
| 5,389,095 | 2/1995 | Suzuki et al. ................................ 604/385.2 |
| 5,435,014 | 7/1995 | Moretz et al. ....................................... 2/403 |
| 5,451,217 | 9/1995 | Fujioka et al. ................................. 604/378 |
| 5,476,458 | 12/1995 | Glaug et al. ..................................... 604/378 |
| 5,486,166 | 1/1996 | Bishop et al. ................................... 604/366 |
| 5,490,846 | 2/1996 | Ellis et al. ....................................... 604/366 |
| 5,531,732 | 7/1996 | Wood ............................................... 604/391 |
| 5,546,607 | 8/1996 | Roberts ................................................ 2/406 |
| 5,575,785 | 11/1996 | Gryskiewicz et al. ...................... 604/385.2 |
| 5,593,400 | 1/1997 | O'Leary .......................................... 604/402 |
| 5,651,779 | 7/1997 | Burrell ............................................. 604/402 |
| 5,827,261 | 10/1998 | Osborn, III ..................................... 604/398 |

DISPOSABLE ABSORBENT ARTICLE HAVING AN ABSORBENT SUPPORT SYSTEM

FIELD OF THE INVENTION

The present invention relates to disposable absorbent articles which are adapted to contain body exudates. More particularly, the present invention relates to disposable absorbent articles which have a loose fitting outer cover which provides a more garment-like appearance.

BACKGROUND OF THE INVENTION

Conventional disposable absorbent articles, such as disposable diapers, have typically included a bodyside liner, an outer cover, and an absorbent core disposed between the outer cover and the bodyside liner. The outer covers of such absorbent articles have been constructed with various types of elasticized portions at the waist and leg opening regions. Such elasticized portions have been used to reduce the leakage of body exudates from the absorbent article and improve the appearance and fit of the absorbent article about the wearer. For example, conventional disposable absorbent articles have generally utilized outer covers which have elastic strands positioned at the leg and waist opening regions to gather the outer cover to hold the absorbent core of the article against the body of the wearer. Typically, the absorbent core of such conventional absorbent articles has been secured to the outer cover and/or bodyside liner at multiple locations along it's length.

However, conventional disposable absorbent articles which are configured as described above have exhibited several shortcomings. For example, it has been difficult to conform conventional absorbent articles and, in particular, the absorbent cores of such articles to the body of the wearer. Typically, the absorbent core on such conventional absorbent articles has been bonded to or immobilized between the outer cover and the bodyside liner and the outer cover has been used to maintain the absorbent core in close proximity to the wearer's body in use. Consequently, it has been difficult to control the shape of the absorbent article to maintain an aesthetically pleasing appearance during use. In an attempt to better gather the absorbent core and the absorbent article, the waist and leg opening regions of conventional absorbent articles have included elastics which apply high contracting or gathering forces on the absorbent article. However, such high forces have undesirably resulted in irritation and red marking of the skin of the wearer. The high forces have also resulted in an undesirable level of bunching of the absorbent article especially in the crotch region.

Several attempts have been made to improve the conformance of such articles to the wearer. For example, some conventional absorbent articles have included absorbent cores which are only attached to the outer cover at their end regions such that the outer cover has a "blousy" appearance and the absorbent core can move and conform to the wearer without being restricted by the outer cover. However, absorbent articles which have included absorbent cores attached to the outer cover at their end margins have not been completely satisfactory. For example, the absorbent cores in such articles have drooped and sagged during use especially after becoming saturated with body exudates. Such sagging and drooping has undesirably resulted in improper fit and appearance which has lead to increased leakage.

Despite the attempts to develop more aesthetically pleasing and improved disposable absorbent articles, there remains the need for disposable absorbent articles which contain body exudates while providing an optimum fit about the wearer and maintaining a pleasing appearance even after becoming saturated. Moreover, there is a need for a disposable absorbent article which has a garment-like appearance and which can be easily secured about and removed from the waist of a wearer.

SUMMARY OF THE INVENTION

In response to the difficulties and problems discussed above, a new disposable absorbent article which has a loose fitting outer cover to provide a more garment-like appearance has been discovered. In one aspect, the present invention concerns a disposable absorbent article which includes an outer cover, an absorbent chassis and an absorbent chassis support member which is attached to the absorbent chassis and which extends between and connects the absorbent chassis to the outer cover. The absorbent chassis includes a pair of longitudinally opposed waist edges which are directly attached to the outer cover and an unattached portion which is not directly attached to the outer cover between the longitudinally opposed waist edges. The absorbent chassis support member includes a strip of material which is directly attached to the unattached portion of the absorbent chassis and the outer cover and extends between the unattached portion of the absorbent chassis and the outer cover. The absorbent chassis support member is configured to maintain the absorbent chassis close to a wearer's body in use. In a particular embodiment, the absorbent chassis support member includes a strip of material which is attached to and extends between a pair of laterally opposed side edges of the outer cover and remains substantially unattached to the outer cover between the side edges.

In another aspect, the present invention concerns a disposable absorbent article which comprises an outer cover, an absorbent chassis and an absorbent chassis support member. The outer cover defines a pair of laterally opposed side edges, a front waist region, a back waist region and a crotch region which extends between and connects the waist regions. The absorbent chassis defines a front attached portion and a back attached portion which are attached to the outer cover and an unattached portion which extends between the attached portions and which remains substantially unattached to the outer cover. The absorbent chassis support member includes a strip of material that is directly attached to and extends between the laterally opposed side edges of the outer cover in the front waist region of the outer cover and is directly attached to the unattached portion of the absorbent chassis. The absorbent chassis support member is configured to maintain the unattached portion of the absorbent chassis close to a wearer's body in use.

In yet another aspect, the present invention concerns a disposable absorbent article which comprises an outer cover, an absorbent chassis, a fastening system and an absorbent chassis support member. The outer cover defines a pair of laterally opposed side edges, a front waist region, a back waist region and a crotch region which extends between and connects the waist regions. The absorbent chassis includes a backsheet, a bodyside liner which is connected to the backsheet in a superposed relation and an absorbent core disposed between the backsheet and the bodyside liner. At least about 90 percent of a length of the absorbent chassis remains substantially unattached to the outer cover. The fastening system includes a pair of primary fasteners located on the laterally opposed side edges of the outer cover in the back waist region of the outer cover and a pair of secondary fasteners on the laterally opposed side edges of the outer cover in the front waist region of the outer cover. The absorbent chassis support member includes a strip of material that is directly attached to the absorbent chassis and extends between and connects the unattached portion of the absorbent chassis to the laterally opposed side edges of the outer cover adjacent the secondary fasteners. The absorbent chassis support member is configured to maintain the absorbent chassis close to a wearer's body in use. The primary fasteners are configured to encircle the wearer's hips and engage an outer surface of the front waist region of the outer cover to maintain the absorbent article about the wearer in use. The secondary fasteners are configured to engage a body facing surface of the absorbent chassis in use.

The present invention advantageously provides a disposable absorbent article which has a garment-like appearance and refastenable side seams which allow the article to be easily secured about and removed from the waist of the wearer. The disposable absorbent article of the different aspects of the present invention also achieves a good fit while maintaining an aesthetically pleasing appearance when compared to conventional absorbent articles which gather and bunch in the crotch region. Moreover, the disposable absorbent article of the present invention provides improved containment of body exudates within the absorbent core of the article by allowing the absorbent core to remain unattached from the outer cover in at least the crotch region of the article and maintaining the absorbent core close to the wearer's body.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention concerns disposable absorbent articles which have a garment-like appearance. The disposable absorbent articles are adapted to be worn adjacent to the body of a wearer to absorb and contain various exudates discharged from the body. As used herein, the term "disposable" refers to articles which are intended to be discarded after a limited use and which are not intended to be laundered or otherwise restored for reuse. The disposable absorbent articles of the present invention will be described in terms of a disposable diaper article which is adapted to be worn by infants about the lower torso. It is understood that the disposable absorbent articles of the present invention are equally adaptable for use as other types of absorbent articles such as adult incontinent products, training pants, feminine hygiene products, other personal care or health care garments, and the like.

Figure 1:
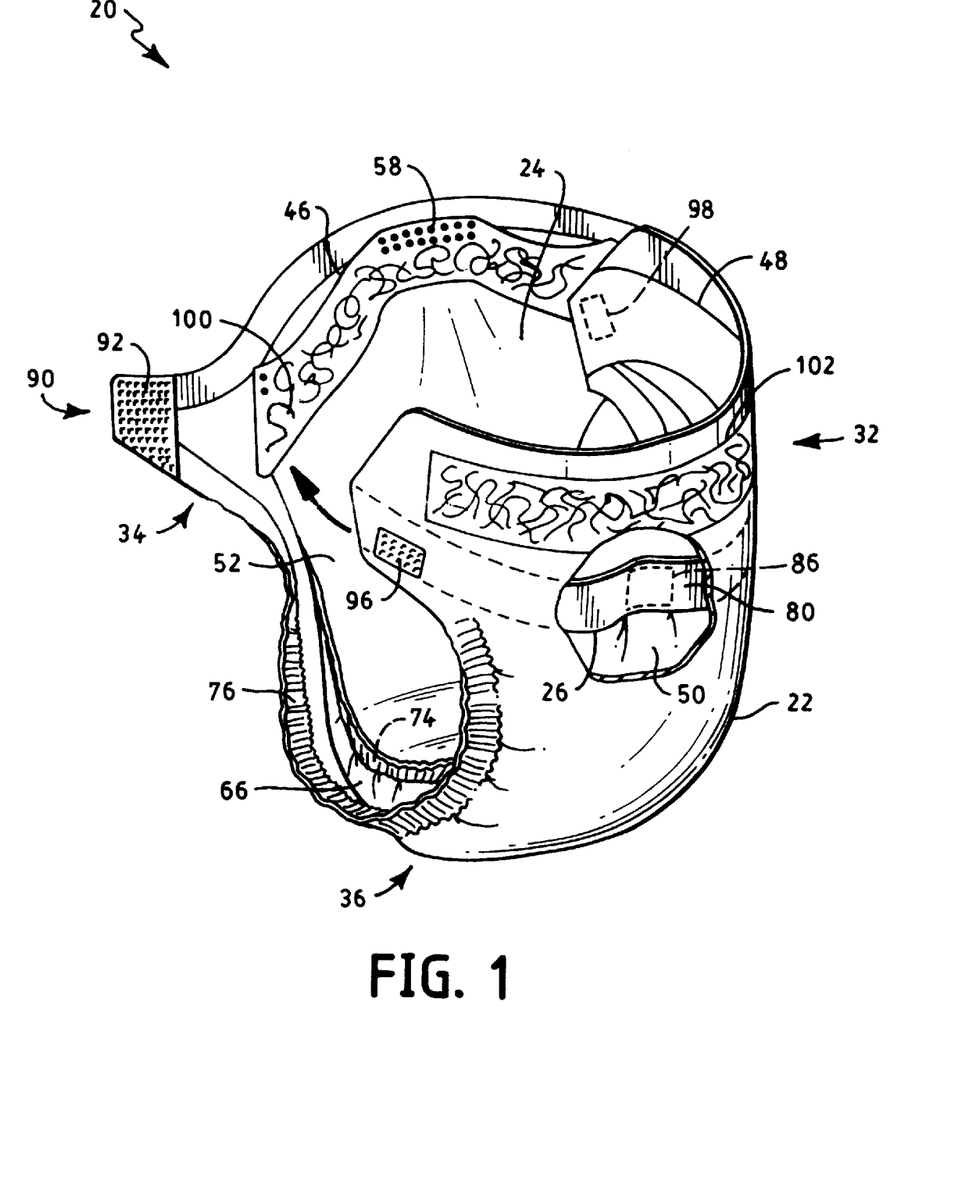
FIG. 1 representatively shows a partially cut-away, perspective view of an example of a disposable absorbent article according to the present invention wherein the elastic members have contracted and gathered the edges of the disposable absorbent article.
Figure 2:
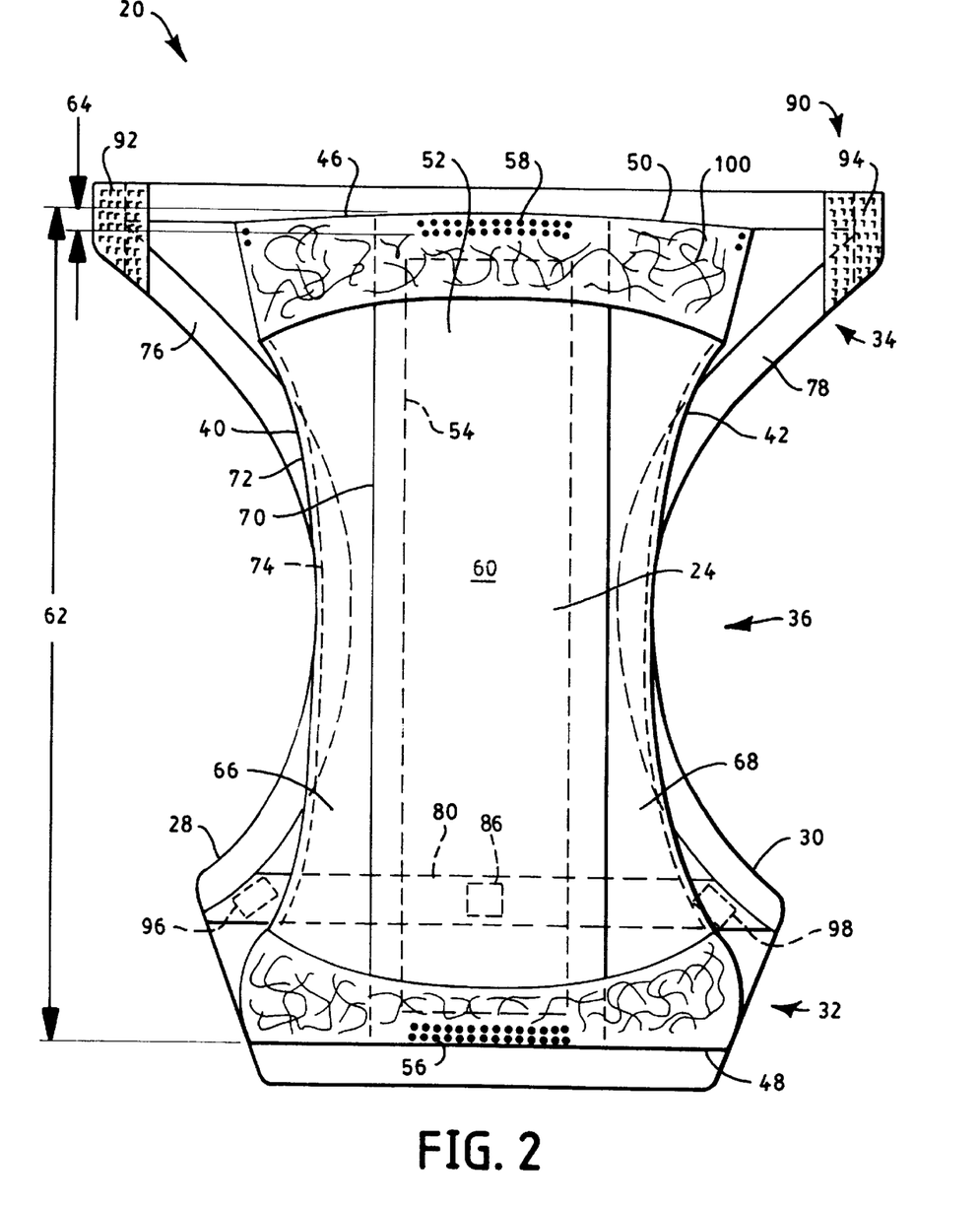
FIG. 2 representatively shows a plan view of the disposable absorbent article of FIG. 1 in a stretched and laid flat condition with the surface of the article which contacts the wearer facing the viewer.
Figure 3:
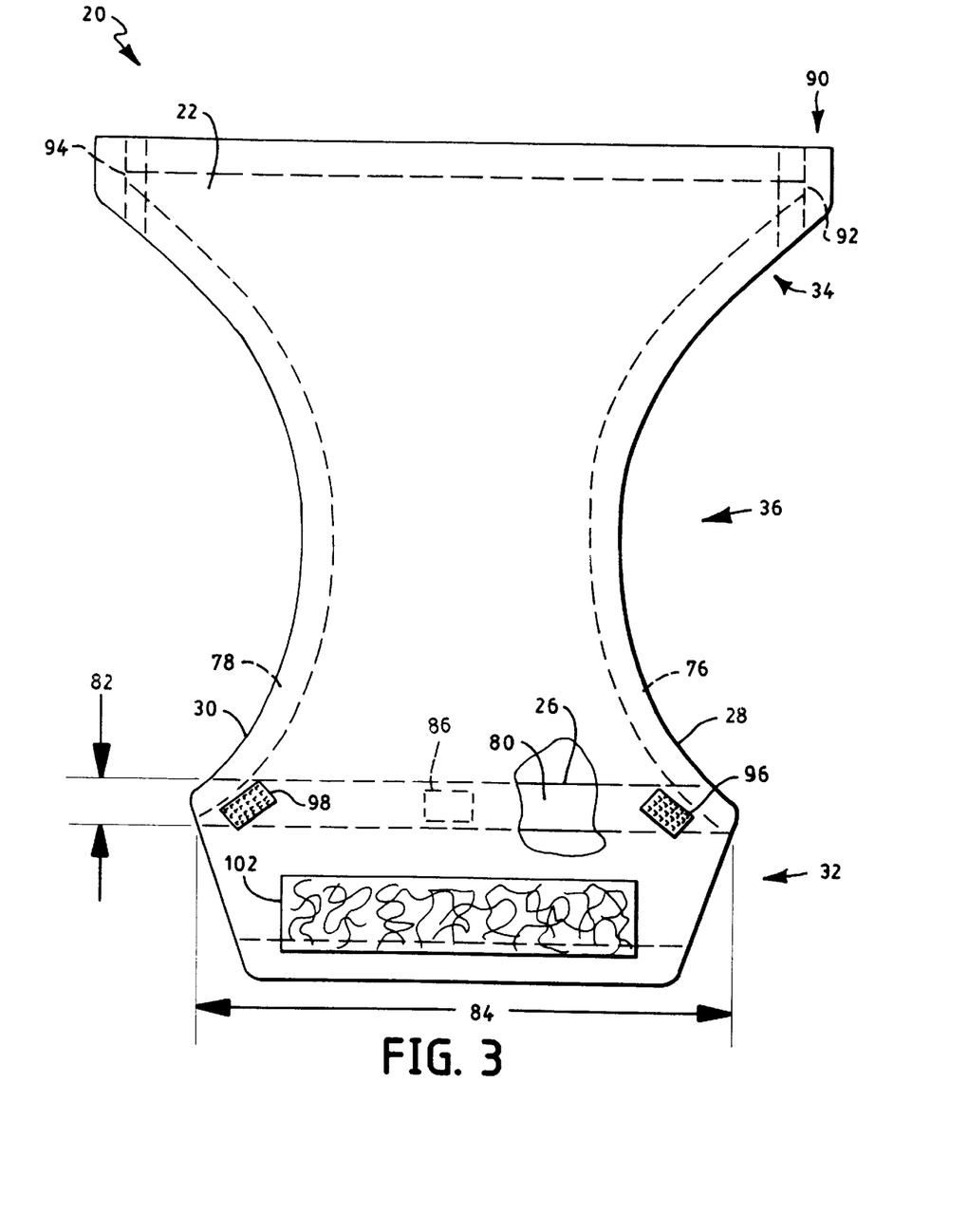
FIG. 3 representatively shows a partially cut-away, plan view of the disposable absorbent article of FIG. 1 in a stretched and laid flat condition with the surface of the article which contacts the wearer's clothing facing the viewer.

FIGS. 1–3 representatively illustrate an example of a disposable diaper, as generally indicated at 20, according to the present invention. As representatively illustrated in FIGS. 1–3, the diaper 20 includes an outer cover 22, an absorbent chassis 24 and an absorbent chassis support member 26 which is connected to and extends between the outer cover 22 and absorbent chassis 24. The absorbent chassis 24 is configured to contain and/or absorb any body exudates discharged from the wearer. Whereas, the outer cover 22 is configured to maintain the diaper 20 about the waist of the wearer, conceal the absorbent chassis 24 from view, and provide a garment-like appearance. The absorbent chassis support member 26 is configured to support and maintain the absorbent chassis 24 in a close, conforming fit to the wearer during use. The illustrated diaper 20 further includes a fastening system 90 which is intended to maintain the diaper 20 about the waist of the wearer when in use. It should be recognized that individual components of the diaper 20 may be optional depending upon the intended use of the diaper 20.

As representatively illustrated in FIGS. 1–3, the outer cover 22 of the diaper 20 defines a pair of laterally opposed side edges 28 and 30, a pair of longitudinally opposed waist regions 32 and 34, and a crotch region 36 which extends between and connects the waist regions. The opposed side edges 28 and 30 of the outer cover 22 define leg openings for the outer cover 22 which may be curvilinear. The waist regions 32 and 34 of the outer cover 22 define a waist opening and are configured to encircle the waist of the wearer when worn. The waist regions 32 and 34 may also be referred to as the front waist region 32 and rear waist region 34. The front waist region 32 comprises the portion of the outer cover 22 which, when worn, is positioned on the front of the wearer while the rear waist region 34 comprises the portion of the outer cover 22 which, when worn, is positioned on the back of the wearer and covers the buttocks of the wearer. The crotch region 36 of the outer cover 22 comprises the portion of the outer cover 22 which, when worn, is positioned between the legs of the wearer and covers the lower torso of the wearer.

The outer cover 22 of the diaper 20 may suitably be composed of a material which is either liquid permeable or liquid impermeable. Since the absorbent chassis 24 of the different aspects of the present invention is designed to contain the body exudates discharged from the wearer, it is generally not necessary that the outer cover 22 be liquid impermeable. For example, the outer cover 22 may include various woven or nonwoven materials such as spunbond material, meltblown material, cotton material, rayon material or combinations thereof such as a spunbond-meltblown-spunbond (SMS) laminate material.

The outer cover 22 may otherwise be at least partially liquid impermeable to further prevent any leakage of body exudates. For example, a typical outer cover 22 can be manufactured from a thin plastic film or other flexible liquid-impermeable material. In a particular aspect, the outer cover 22 may be formed from a polyethylene film having a thickness of from about 0.012 millimeter (0.5 mil) to about 0.051 millimeter (2.0 mils). The outer cover 22 may also be formed of a woven or nonwoven fibrous web layer which has been totally or partially constructed or treated to impart a desired level of liquid impermeability to selected regions. Further, the outer cover 22 may optionally be composed of a micro-porous "breathable" material which permits vapors to escape from the diaper 20 while still preventing liquid exudates from passing through the outer cover 22. Still further, the outer cover 22 may also be an elasticized material such as a stretch-thermal laminate (STL), neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference.

If it is desired to present the outer cover 22 with a more clothlike feeling, the outer cover 22 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). The outer cover 22 may otherwise be a stretch-thermal laminate (STL) material which includes a film layer positioned between two spunbond layers and which has a basis weight of about 73 grams per square meter. The film layer may be composed of meltblown polypropylene fibers and the spunbond layers may be composed of polypropylene fibers. The outer cover 22 may also include bicomponent fibers such as polyethylene/polypropylene bicomponent fibers. Methods of forming such clothlike outer covers are known to those skilled in the art.

The outer cover 22 of the diaper 20 may also include a pair of concealment cuffs (not shown) which are configured to hide the absorbent chassis 24 and provide an additional barrier to the lateral flow of body exudates. The concealment cuffs may be located along the laterally opposed side edges 28 and 30 of the outer cover 22. The construction of such concealment cuffs is generally known to those skilled in the art. For example, the concealment cuffs may be constructed of a material which is similar to the material comprising the outer cover 22 and may be attached to the side edges 28 and 30 of the outer cover 22 to effectively hide or conceal the absorbent chassis 24 from view. Generally, each concealment cuff includes a fixed edge which is attached to the side edges 28 and 30 of the outer cover 22 and a free edge which tends to position itself in a spaced relation away from the outer cover 22 toward a generally upright and perpendicular configuration, especially in the crotch region 36 when in use. Desirably, the free edge of each concealment cuff maintains a contacting relationship with the body of the wearer while the outer cover 22 may be spaced away from the body of the wearer when in use. Typically, an elastic member is attached to the free edge of each concealment cuff to maintain the spaced away relationship between the free edge and the outer cover 22.

As representatively illustrated in FIGS. 1–3, the absorbent chassis 24 of the diaper 20 of the present invention defines a pair of laterally opposed side edges 40 and 42 and a pair of longitudinally disposed waist edges 46 and 48. The absorbent chassis 24 according to the present invention may also include a backsheet 50, a bodyside liner 52 which is connected to the backsheet 50 in a superposed relation, and an absorbent core 54 which is located between the bodyside liner 52 and the backsheet 50. The backsheet 50 is typically configured to hold the absorbent chassis 24 of the diaper 20 close to the body of the wearer. In alternative configurations wherein the outer cover 22 of the diaper 20 is at least partially resistant to the flow of liquids therethrough, the backsheet 50 may optionally be omitted from the absorbent chassis 24. The absorbent chassis 24 also defines a longitudinally extending length 62.

The absorbent chassis 24 is generally conformable and capable of absorbing and retaining body exudates. The absorbent chassis 24 may have any of a number of shapes and sizes. For example, the absorbent chassis 24 may be rectangular, I-shaped or T-shaped. The size and absorbent capacity of the absorbent chassis 24 should be compatible with the size of the intended wearer and the fluid loading imparted by the intended use of the diaper 20. Typically, it is desirable that the absorbent chassis 24 have an absorbent capacity of at least about 300 grams of urine. It is generally preferred that the absorbent chassis 24 be narrower in the crotch region 36 than in the waist regions 32 and 34. It has been found that the absorbent chassis 24 of the present invention is particularly useful when the width dimension in the crotch region 36 is from about 2.5 to about 10.2 centimeters (1.0 to about 4.0 inches), desirably no more than about 7.6 centimeters (3.0 inches) and more desirably no more than about 5.1 centimeters (2.0 inches). The narrow crotch width dimension of the absorbent chassis 24 allows the absorbent chassis 24 to better fit between the legs of the wearer.

The absorbent chassis 24 of the present invention is suitably connected to the outer cover 22 to provide the disposable diaper 20. As representatively illustrated in FIGS. 1–3, the absorbent chassis 24 is desirably connected to the outer cover 22 only at or adjacent the waist edges 46 and 48 of the absorbent chassis 24 thereby creating a front attached portion 56, a back attached portion 58 and an unattached portion 60 which extends between and connects the attached portions 56 and 58. The unattached portion 60 of the absorbent chassis 24 remains substantially unattached to the outer cover 22 and is generally configured to fit between the legs of the wearer and at least partially cover the lower torso of the wearer when in use. As a result, the unattached portion 60 is generally the portion of the absorbent chassis 24 which is configured to initially receive the body exudates from the wearer when in use.

The absorbent chassis 24 is connected to the outer cover 22 in such a manner to secure the chassis 24 in place while not adversely restricting the movement of the outer cover 22 in use. For example, the absorbent chassis 24 may be connected to the outer cover 22 along a longitudinal length 64 of no more than about 5.1 centimeters and desirably no more than about 1.3 centimeters at each of the waist edges 46 and 48 of the absorbent chassis 24. In a further aspect, the absorbent chassis 24 is connected to the outer cover 22 such that the unattached portion 60 of the absorbent chassis 24 defines a longitudinal length of at least about 90 percent and desirably at least about 95 percent of a total length 62 of the absorbent chassis 24. In such a configuration, the absorbent chassis 24 more readily conforms to the body and movements of the wearer in use without adversely affecting the garment-like appearance of the outer cover 22. In a particular aspect, the longitudinal length of the unattached portion 60 of the absorbent chassis 24 is less than the longitudinal length of the outer cover 22 between the attached portions 56 and 58. In such a configuration, the absorbent chassis 24 maintains a spaced away relationship from the outer cover 22 in at least the crotch region 36 when in use.

The absorbent chassis 24 may be suitably connected to the outer cover 22 to form the diaper 20 using any means known to those skilled in the art. For example, the absorbent chassis 24 may be bonded to the outer cover 22 using adhesive, thermal or ultrasonic bonding techniques known to those skilled in the art. Alternatively, the absorbent chassis 24 may be connected to the outer cover 22 using conventional fasteners such as buttons, hook and loop type fasteners, adhesive tape fasteners, and the like. The other components of the diaper 20 may be suitably connected together using similar means.

As representatively illustrated in FIGS. 1–3, the disposable absorbent article of the different aspects of the present invention also includes an absorbent chassis support member 26 which is connected to and extends between the outer cover 22 and absorbent chassis 24. The absorbent chassis support member 26 is configured to support and maintain the absorbent chassis 24 and, in particular, the unattached portion 60 of the absorbent chassis 24 in a close, conforming fit to the wearer during use. The absorbent chassis support member 26 can comprise any member which is capable of supporting and maintaining the fit of the absorbent chassis 24 during use and, in particular, after the absorbent core 54 of the chassis 24 has been saturated with body exudates.

For example, as representatively illustrated in FIGS. 1–3, the absorbent chassis support member 26 may include a strip of material 80 which is attached to and extends laterally between the absorbent chassis 24 and the outer cover 22 of the diaper 20. The strip of material 80 may be attached to the absorbent chassis 24 and outer cover 22 at any location which supports the absorbent chassis 24 such as, for example, at location 86 in FIGS. 1–3. Desirably, the strip of material 80 is attached to and extends laterally between the laterally opposed side edges 28 and 30 of the outer cover 22 in one of the waist regions 32 and 34 of the outer cover 22 to better distribute the forces exerted by the absorbent chassis 24 on the outer cover 22. The strip of material 80 may remain substantially unattached from the outer cover 22 between the side edges 28 and 30. Desirably, at least about 85 percent of the lateral, cross-directional length of the strip of material 80 remains unattached to the outer cover 22 such that the strip of material 80 and the weight of the absorbent chassis 24 does not adversely affect the appearance of the outer cover 22. As representatively illustrated in FIGS. 1–3, a portion of the strip of material 80 which extends between the side edges 28 and 30 and which remains unattached to the outer cover 22 is attached to the backsheet 50 of the absorbent chassis 24. Thus, the weight of the absorbent chassis 24 and, in particular, the weight of the unattached portion 60 of the absorbent chassis 24 is supported by the strip of material 80.

The absorbent chassis support member 26 may include a single strip of material 80 in one of the waist regions 32 and 34 of the diaper 20 or may include a strip of material 80 in both waist regions 32 and 34 of the diaper to provide additional support of the absorbent chassis 24. As illustrated in FIGS. 1–3, the absorbent chassis support member 26 desirably includes at least one strip of material 80 in the front waist region 32 of the diaper 20 to support at least the front portion of the absorbent chassis 24 which typically receives the majority of fluid exudates. The strip of material 80 may have any desired shape and size which provides the support of the absorbent chassis 24. For example, as representatively illustrated in FIGS. 1–3, the strip of material 80 may define a width 82 of from about 2 to about 5 centimeters and a length 84 of from about 15 to about 30 centimeters.

The absorbent support member 26, as representatively illustrated in FIGS. 1–3, may suitably be composed of any material which is capable of providing the desired support of the absorbent chassis 24. It is generally preferred that the absorbent support member be formed from a material which is inexpensive, strong and flexible. For example, a typical support member 26 can be manufactured from a thin plastic film or other flexible nonwoven material. For example, the support member 26 may be formed from a polyethylene film having a thickness of from about 0.012 millimeter (0.5 mil) to about 0.051 millimeter (2.0 mils). The support member 26 may otherwise comprise a nonwoven web material, such as a meltblown or spunbond web of polyolefin fibers. Further, the support member 26 may optionally be composed of an elastic or stretchable material which permits the support member 26 to stretch as forces are exerted on it due to the weight of the absorbent chassis 24.

The bodyside liner 52 of the absorbent chassis 24, as representatively illustrated in FIGS. 1–3, suitably presents a bodyfacing surface which is intended to be worn adjacent the body of the wearer and is compliant, soft feeling and nonirritating to the wearer's skin. Further, the bodyside liner 52 may be less hydrophilic than the absorbent core 54, to present a relatively dry surface to the wearer, and may be sufficiently porous to be liquid permeable, permitting liquid to readily penetrate through its thickness. A suitable bodyside liner 52 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 52 is suitably employed to help isolate the wearer's skin from fluids held in the absorbent core 54 of the absorbent chassis 24.

Various woven and nonwoven fabrics can be used for the bodyside liner 52. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 52 comprises a nonwoven, spunbond, polypropylene fabric composed of about 2.8–3.2 denier fibers formed into a web having a basis weight of about 22 grams per square meter and a density of about 0.06 grams per cubic centimeter. The fabric is surface treated with about 0.28 weight percent of a surfactant commercially available from Rohm and Haas Co. under the trade designation TRITON X-102.

The backsheet 50 of the absorbent chassis 24, as representatively illustrated in FIGS. 1–3, may suitably be composed of a material which is either liquid permeable or liquid impermeable. It is generally preferred that the backsheet 50 be formed from a material which is substantially impermeable to fluids. For example, a typical backsheet can be manufactured from a thin plastic film or other flexible liquid-impermeable material. For example, the backsheet 50 may be formed from a polyethylene film having a thickness of from about 0.012 millimeter (0.5 mil) to about 0.051 millimeter (2.0 mils). The backsheet 50 may also comprise a film layer having a nonwoven web laminated to the outer surface thereof, such as a spunbond web of polyolefin fibers. The backsheet 50 may also be constructed of a material which is similar to the material comprising the outer cover 22, such as an STL material. Further, the backsheet 50 may be formed of a woven or nonwoven fibrous web layer which has been totally or partially constructed or treated to impart a desired level of liquid impermeability to selected regions that are adjacent or proximate the absorbent core 54. Still further, the backsheet 50 may optionally be composed of a micro-porous "breathable" material which permits vapors to escape from the absorbent core 54 while still preventing liquid exudates from passing through the backsheet 50.

The bodyside liner 52 and backsheet 50 are generally adhered to one another so as to form a pocket in which the absorbent core 54 is located to provide the absorbent chassis 24. The bodyside liner 52 and backsheet 50 may be adhered directly to each other around the outer periphery of the absorbent chassis 24 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 52 to the backsheet 50. It should be noted that both the bodyside liner 52 and the backsheet 50 need not extend completely to the outer periphery of the absorbent chassis 24. For example, the backsheet 50 may extend to the outer periphery of the absorbent chassis 24 while the bodyside liner 52 may be attached to the backsheet 50 inboard of the outer periphery of the absorbent chassis 24, or more towards the longitudinal centerline of the diaper 20. In alternative configurations, especially wherein the backsheet 50 is omitted, the bodyside liner 52 may be suitably adhered directly to the absorbent core 54.

The absorbent core 54, as representatively illustrated in FIGS. 1–3, is positioned between the bodyside liner 52 and the backsheet 50 to form the absorbent chassis 24. The absorbent core 54 is desirably conformable and capable of absorbing and retaining body exudates. The absorbent core 54 may have any of a number of shapes and sizes. For example, the composite absorbent core may be rectangular, I-shaped or T-shaped. It is generally preferred that the absorbent core 54 be narrower in the crotch region 36. The size of the absorbent core 54 should be compatible with the size of the intended wearer and the desired absorbent capacity of the absorbent chassis 24.

In a particular embodiment, as representatively illustrated in FIGS. 1–3, the absorbent core 54 of the absorbent chassis 24 is desirably a plurality of absorbent strips which extend along the longitudinal length 62 of the absorbent chassis 24. The absorbent strips are generally rectangular in shape and define a length, a width, a thickness and a pair of opposite longitudinal side edges. The absorbent strips are configured to pivot about one of the longitudinal side edges while the opposite longitudinal side edge of the absorbent strips remains free to move. The absorbent core 54 may include any number of absorbent strips which provides the desired containment of body exudates. For example, the absorbent core 54 may include four longitudinally extending absorbent strips. In alternative configurations, the absorbent core 54 may include from 1 to 10 absorbent strips. The arrangement of the absorbent strips provides channels between each strip to better distribute and contain fluid exudates. Moreover, the arrangement of the strips provides a greater surface area in contact with the body exudates than conventional planar absorbent cores to more effectively absorb and contain the exudates. The absorbent strips are also very conformable in the crotch section of the absorbent chassis 24. For example, the absorbent strips are arranged such that they may overlap each other in a shingled arrangement when subjected to a lateral force such as exerted by the legs of a wearer in use. Various configurations for the absorbent strips are described in U.S. patent application Ser. No. 08/476,742 of S. Gryskiewicz et al., entitled ABSORBENT ARTICLE INCLUDING LIQUID CONTAINMENT BEAMS AND LEAKAGE BARRIERS, and filed Jun. 7, 1995 (Attorney Docket No. 12,187); the disclosure of which is hereby incorporated by reference in a manner that is consistent herewith.

The absorbent core 54 of the absorbent chassis 24 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 54 may also comprise selected blends of the various types of fibers mentioned above.

In a particular aspect of the invention, the absorbent core 54 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 54 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 54 may comprise a laminate of fibrous webs and high-absorbency material or other suitable means of maintaining a high-absorbency material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like. Conglomerates of particles of high-absorbency material may also be used. An example of a superabsorbent polymer suitable for use in the present invention is a superabsorbent polymer designated IM5000 which is commercially available from Hoechst-Celanese, a business having offices in Portsmouth, Va. Other suitable high-absorbency materials may include superabsorbent polymers which are commercially available from Dow Chemical Corp., a business having offices in Midland, Mich.

As a general rule, the high-absorbency material is present in the absorbent core 54 of the present invention in an amount of from about 5 to about 95 weight percent and desirably from about 10 to about 60 weight percent based on the total weight of the absorbent core 54. The distribution of the high-absorbency material within the different portions of the absorbent core 54 can vary depending upon the intended end use of the absorbent core 54.

As representatively illustrated in FIGS. 1–3, the absorbent chassis 24 of the disposable diaper 20 may include a pair of containment flaps 66 and 68 which are configured to provide a barrier to the lateral flow of body exudates. The containment flaps 66 and 68 may be located along the laterally opposed side edges 40 and 42 of the absorbent chassis 24. Each containment flap defines an attached edge 70 and an unattached edge 72. Each of the containment flaps 66 and 68 may also include at least one elongated elastic member 74 which is adhered to the unattached edge 72 of the containment flap 66 and 68 and configured to gather the unattached edge 72 and form a seal against the body of the wearer when in use. The containment flaps 66 and 68 may extend longitudinally along the entire length 62 of the absorbent chassis 24 or may only extend partially along the length of the absorbent chassis 24. When the containment flaps 66 and 68 are shorter in length than the absorbent chassis 24, the containment flaps 66 and 68 can be selectively positioned anywhere along the side edges 40 and 42 of the absorbent chassis 24. In a particular aspect of the invention, the containment flaps 66 and 68 extend along the entire length 62 of the absorbent chassis 24 to better contain the body exudates.

The containment flaps 66 and 68 can be made from any material which provides the desired barrier against the flow of body exudates. For example, the containment flaps 66 and 68 may be constructed of a material which is similar to the material comprising the outer cover 22. Other conventional materials, such as polymeric films, may also be employed. The material for the containment flaps 66 and 68 may also be liquid resistant and/or gas permeable for improved performance. In a particular aspect, the containment flaps 66 and 68 may be constructed of a STL material having a basis weight of about 73 grams per square meter and comprising a meltblown layer of meltblown polypropylene fibers between two spunbond layers of polypropylene fibers.

Each containment flap 66 and 68 is attached to the side edges 40 and 42 of the absorbent chassis 24 such that the containment flaps 66 and 68 provide a barrier to the lateral flow of body exudates. The attached edge 70 of each of the containment flaps 66 and 68 is attached to the side edges 40 and 42 of the absorbent chassis 24 while the unattached edge 72 remains unattached from the absorbent chassis 24 in at least the crotch region 36 of the absorbent chassis 24. The attached edge 70 of the containment flaps 66 and 68 may be attached to the absorbent chassis 24 in any of several ways which are well known to those skilled in the art. For example, the attached edge 70 of the flaps 66 and 68 may be ultrasonically bonded, thermally bonded or adhesively bonded to the outer cover 22. In a particular aspect, the unattached edge 72 of each of the containment flaps 66 and 68 remains unattached from the side edges 40 and 42 of the absorbent chassis 24 along substantially the entire length of the unattached edge 72 to provide improved performance.

Alternatively as representatively illustrated in FIGS. 1–3, the containment flaps 66 and 68 may be integral with the backsheet 50 of the absorbent chassis 24. For example, the containment flaps 66 and 68 may be composed of portions of the backsheet 50 which extend laterally beyond the side edges 40 of the absorbent core 54 of the absorbent chassis 24.

Each containment flap 66 and 68 is also configured such that the unattached edge 72 of the containment flap 66 and 68 tends to position itself in a spaced relation away from the absorbent chassis 24 toward a generally upright and perpendicular configuration, especially in the crotch region 36 when in use. As representatively illustrated in FIGS. 1–3, the unattached edge 72 of each containment flap 66 and 68 is desirably spaced away from the absorbent chassis 24 when in use thereby providing a barrier to the lateral flow of body exudates. Desirably, the unattached edge 72 of each containment flap 66 and 68 maintains a contacting relationship with the body of the wearer while the absorbent chassis 24 may be spaced away from the body of the wearer when in use. Typically, an elastic member 74 is attached to the unattached edge 72 of each containment flap 66 and 68 to maintain the spaced away relationship between the unattached edge 72 and the absorbent chassis 24. For example, the elastic member 74 may be attached to the unattached edge 72 in an elastically contractible condition such that the contraction of the elastic member 74 gathers or contracts and shortens the unattached edge 72 of the containment flap 66 and 68.

Materials suitable for use as the elastic member 74 of the containment flaps 66 and 68 are known to those skilled in the art. Exemplary of such materials are sheets, strands or ribbons of a polymeric, elastomeric material which are adhered to the flaps 66 and 68 in a stretched condition, or which are attached to the flaps 66 and 68 while the flaps are pleated, such that elastic constrictive forces are imparted to the flaps. The elastic member 74 may also include such materials as polyurethane, synthetic and natural rubber. In a particular aspect of the invention, the elastic members 74 may be composed of a plurality of individual strands of 620 decitex LYCRA elastomer which are commercially available from E. I. DuPont de Nemours Co. The containment flaps 66 and 68 may include from 1 to 10 elastic strands along the unattached edge 72. The elastic members 74 may be elongated prior to being attached to the unattached edge 72 of the containment flaps 66 and 68. For example, the elastic members 74 may be elongated at least about 75 percent and desirably from about 100 to about 150 percent before being attached such that the elastic members 74 gather the unattached edge 72 of the containment flaps 66 and 68. Desirably, the elastic members 74 are configured to gather and maintain the unattached edge 72 in a contacting relationship with the wearer's body when in use to effectively provide a seal against the lateral flow of body exudates.

Alternative constructions and arrangements for containment flaps 66 and 68 are described in U.S. Pat. No. 4,704,116 issued Nov. 3, 1987, to K. Enloe the disclosure of which is hereby incorporated by reference in a manner that is consistent herewith. The absorbent article of the different aspects of the present invention further includes a fastening system 90 for securing the absorbent article about the waist of the wearer. Typically, the fastening system 90 includes fasteners which are located on the outer cover 22 of the diaper 20 and which are configured to be refastenable. The use of fasteners which are refastenable or releasably engageable allows for ease of securing and removing the diaper 20 from the waist of the wearer.

For example, the fastening system 90 of the present invention, as representatively illustrated in FIGS. 1–3, includes a pair of primary fasteners 92 and 94 which are located on the outermost corners of the back waist region 34 of the outer cover 22. The primary fasteners 92 and 94 are configured to encircle the hips of the wearer and engage an outer surface of the front waist region 32 of the outer cover 22 for holding the diaper 20 on the wearer. Desirably, as representatively illustrated in FIGS. 1–3, the primary fasteners 92 and 94 are releasably engageable directly with the outer surface of the outer cover 22 to provide improved ease of fastening. Alternatively, the disposable diaper 20 of the present invention may include a fastening panel 102 on the outer surface of the front waist region 32 of the outer cover 22. In such a configuration, the primary fasteners 92 and 94 are releasably engageable with the fastening panel 102 to maintain the diaper 20 about the waist of the wearer. When the primary fasteners 92 and 94 are releasably engaged, the side edges 28 and 30 of the outer cover 22 encircle the legs of the wearer thereby defining the leg openings.

Suitable fasteners are well known to those skilled in the art and can include tape tab fasteners, hook and loop fasteners, mushroom fasteners, snaps, pins, belts and the like, and combinations thereof. For example, as representatively illustrated in FIGS. 1–3, the primary fasteners 92 and 94 may be hook type fasteners and the outer cover 22 or fastening panel may be configured to function as a complimentary loop type fastener.

Desirably, the primary fasteners 92 and 94 are hook type fasteners which are releasably engageable with the outer cover 22. Such an arrangement provides the ability to vary the size of the waist opening in very small increments over a wide range to fit the waist of the wearer. The primary fasteners 92 and 94 may have any shape and size which provides the desired fastening of the diaper 20 about the waist of the wearer.

The fastening system 90 on the disposable diaper 20 of the present invention may further include a pair of secondary fasteners 96 and 98 to provide improved securement of the diaper 20 about the waist of the wearer and to provide additional support to maintain the absorbent chassis 24 in contact with the wearer. For example, as representatively illustrated in FIGS. 1–3, the diaper 20 may include a pair of secondary fasteners 96 and 98 which are located on the side edges 28 and 30 of the front waist region 32 of the outer cover 22. The secondary fasteners 96 and 98 are configured to encircle the hips of the wearer and engage a bodyfacing surface 100 of the rear waist edge 48 of the absorbent chassis 24 to maintain the absorbent chassis 24 of the diaper 20 in a close conforming fit to the buttocks of the wearer. Desirably, as representatively illustrated in FIGS. 1–3, the secondary fasteners 96 and 98 are hook type fasteners which are releasably engageable directly with the bodyfacing surface 100 of the absorbent chassis 24 to provide improved ease of fastening. Alternatively, the disposable diaper 20 of the present invention may include one or more fastening panels (not shown) on the bodyfacing surface of the rear waist edge 48 of the absorbent chassis 24 to which the secondary fasteners 96 and 98 are releasably engageable. When the secondary fasteners 96 and 98 are releasably engaged, the absorbent chassis 24 is supported by both the absorbent support member 26 and the secondary fasteners 96 and 98 to ensure the absorbent chassis 24 remains in close contact with the wearers buttocks in use.

Desirably, the absorbent support member 26, as discussed above and representatively illustrated in FIGS. 1–3, is attached to the side edges 28 and 30 of the outer cover 22 at or adjacent the location of the fasteners 92 and 94 or 96 and 98. For example, as illustrated in FIGS. 1–3, the absorbent support member 26 may include a strip of material 80 whose ends have been attached to the side edges 28 and 30 of the outer cover 22 adjacent the location of the secondary fasteners 96 and 98. In such a configuration, the forces exerted on the support member 26 are transferred to the fasteners 96 and 98 which more evenly distribute the forces to the rest of the diaper 20. In particular, the forces are distributed through the fasteners to the waist regions and leg regions of the outer cover 22.

The disposable diaper 20 of the different aspects of the present invention may further include elastics at the waist edges and side edges 30 and 32 of the outer cover 22 to further prevent the leakage of body exudates and support the absorbent chassis 24. For example, as representatively illustrated in FIGS. 1–3, the diaper 20 of the present invention may include a pair of leg elastic members 76 and 78 which are which are connected to the laterally opposed side edges 28 and 30 in the crotch region 36 of the outer cover 22. The leg elastics 76 and 78 are generally adapted to fit about the legs of a wearer in use to maintain a positive, contacting relationship with the wearer to effectively reduce or eliminate the leakage of body exudates from the diaper 20.

Materials suitable for use as the leg elastics 76 and 78 are well known to those skilled in the art. Exemplary of such materials are sheets or strands or ribbons of a polymeric, elastomeric material which are adhered to the outer cover 22 in a stretched position, or which are attached to the outer cover 22 while the outer cover is pleated, such that elastic constrictive forces are imparted to the outer cover 22. The leg elastics may also include such materials as polyurethane, synthetic and natural rubber. In a particular aspect of the invention, the elastics may be composed of individual strands of 620 decitex LYCRA elastomer which are commercially available from E. I. DuPont de Nemours Co. When individual strands of elastic are used, the waist and leg elastics may include any suitable number of elastic strands to provide containment of the body exudates. For example, the leg elastics 76 and 78 may include from 1 to 10 elastic strands. The leg elastics may be elongated prior to being attached to the outer cover 22. For example, the leg elastics may be elongated at least about 150 percent and desirably from about 200 to about 500 percent before being attached such that the elastics gather the outer cover 22 when relaxed. The leg elastics 76 and 78 may be joined to the outer cover 22 by any means known to those skilled in the art. For example, adhesive, thermal or ultrasonic bonding techniques may be used to join the elastics to the outer cover. Suitable adhesives include Findley H-2096 or H2525A hot melt adhesives which are commercially available from Findley Adhesives, Inc.

The different aspects of the present invention can advantageously provide a disposable absorbent article which has an absorbent chassis that maintains a close conforming fit with the wearer. The absorbent article also has a garment-like appearance. As a result, the disposable absorbent article of the present invention effectively contains body exudates while maintaining an optimum fit and an aesthetically pleasing appearance. Moreover, the crotch region of the disposable absorbent article of the present invention does not sag or droop as conventional absorbent articles have after becoming saturated with body exudates. As a result, the absorbent article may have a reduced level of leakage. While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A disposable absorbent article which comprises an outer cover, an absorbent chassis which includes a pair of longitudinally opposed waist edges which are directly attached to said outer cover and an unattached portion which is not directly attached to said outer cover between said longitudinally opposed waist edges and an absorbent chassis support member which includes a strip of material which is directly attached to said outer cover and said unattached portion of said absorbent chassis and which extends between said unattached portion of said absorbent chassis and said outer cover wherein said absorbent chassis support member is configured to maintain said absorbent chassis close to a wearer's body in use.

2. The absorbent article of claim 1 wherein said outer cover is a nonwoven material.

3. The absorbent article of claim 1 wherein said outer cover defines a pair of laterally opposed side edges, a front waist region, a back waist region and a crotch region which extends between and connects said waist regions and wherein said absorbent article further comprises a pair of leg elastics which are respectively located on said pair of laterally opposed side edges of said outer cover in at least said crotch region of said outer cover.

4. The absorbent article of claim 1 wherein said longitudinally opposed waist edges of said absorbent chassis are attached to said outer cover along a longitudinal length of no more than about 5.1 centimeters.

5. The absorbent article of claim 1 wherein said absorbent chassis defines a longitudinally extending length and said absorbent chassis remains unattached from said outer cover for at least about 90 percent of said length.

6. The absorbent article of claim 1 wherein said absorbent article further comprises a pair of longitudinally extending containment flaps which are respectively located on a pair of laterally opposed side edges of said absorbent chassis.

7. The absorbent article of claim 6 wherein each of said containment flaps defines an attached edge and an unattached edge which remains unattached to said absorbent chassis in at least a crotch region of said absorbent article.

8. The absorbent article of claim 7 wherein said unattached edge of each of said containment flaps includes at least one elastic member which is configured to maintain said unattached edge in a spaced away relationship from said absorbent chassis in at least said crotch region.

9. The absorbent article of claim 6 wherein each of said containment flaps extends along substantially an entire length of said absorbent chassis.

10. The absorbent article of claim 6 wherein said absorbent chassis includes a backsheet and an absorbent core and wherein each of said containment flaps are provided by a portion of said backsheet which extends laterally beyond said absorbent core.

11. The absorbent article of claim 1 wherein said strip of material is attached to and extends between a pair of laterally opposed side edges of said outer cover and remains substantially unattached to said outer cover between said side edges.

12. The absorbent article of claim 11 wherein said strip of material defines a width of from about 2 to about 5 centimeters.

13. The absorbent article of claim 11 wherein at least about 85 percent of a lateral, cross directional length of said strip of material remains unattached to said outer cover.

14. The absorbent article of claim 11 wherein a portion of said strip of material which remains unattached to said outer cover is attached to said absorbent chassis to maintain said absorbent chassis close to said wearer's body in use.

15. The absorbent article of claim 1 wherein said absorbent chassis support member is connected to a front waist region of said outer cover.

16. A disposable absorbent article which comprises:

a) an outer cover which defines a pair of laterally opposed side edges, a front waist region, a back waist region and a crotch region which extends between and connects said waist regions;

b) an absorbent chassis which defines a total length, a front attached portion and a back attached portion which are directly attached to said outer cover and an unattached portion which extends between and connects said attached portions and which is not directly attached to said outer cover; and c) an absorbent chassis support member which includes a strip of material which is directly attached to and extends between said laterally opposed side edges of said outer cover in said front waist region of said outer cover and which is directly attached to said unattached portion of said absorbent chassis wherein said absorbent chassis support member is configured to maintain said unattached portion of said absorbent chassis close to a wearer's body in use.

17. The absorbent article of claim 16 wherein said outer cover is a nonwoven material.

18. The absorbent article of claim 16 wherein said absorbent article further comprises a pair of leg elastics which are respectively located on said pair of laterally opposed side edges of said outer cover in at least said crotch region of said outer cover.

19. The absorbent article of claim 16 wherein each of said attached portions of said absorbent chassis define a longitudinal length of no more than about 5.1 centimeters.

20. The absorbent article of claim 16 wherein said unattached portion of said absorbent chassis defines a longitudinal length of at least about 90 percent of said total length of said absorbent chassis.

21. The absorbent article of claim 16 wherein said absorbent article further comprises a pair of longitudinally extending containment flaps which are respectively located on a pair of laterally opposed side edges of said absorbent chassis.

22. The absorbent article of claim 21 wherein each of said containment flaps are provided by a portion of a backsheet of said absorbent chassis which extends laterally beyond an absorbent core of said absorbent chassis.

23. The absorbent article of claim 16 wherein said absorbent chassis support member remains substantially unattached to said outer cover between said side edges of said outer cover.

24. The absorbent article of claim 23 wherein a portion of said absorbent chassis support member which remains unattached to said outer cover is attached to said absorbent chassis to maintain said absorbent chassis close to said wearer's body in use.

25. The absorbent article of claim 16 wherein said absorbent chassis support member is a strip of nonwoven material which defines a width of from about 2 to about 5 centimeters.

26. A disposable absorbent article which comprises:
 a) an outer cover which defines a pair of laterally opposed side edges, a front waist region, a back waist region and a crotch region which extends between and connects said waist regions;
 b) an absorbent chassis which includes a pair of longitudinally opposed waist edges which are directly attached to said outer cover, a backsheet, a bodyside liner which is connected to said backsheet in a superposed relation and an absorbent core disposed between said backsheet and said bodyside liner wherein at least about 90 percent of a longitudinal length of said absorbent chassis is not directly attached to said outer cover to define an unattached portion between said waist edges;
 c) a fastening system which includes a pair of primary fasteners located on said laterally opposed side edges of said outer cover in one of said waist regions of said outer cover and a pair of secondary fasteners located on said laterally opposed side edges in said opposite waist region of said outer cover; and
 d) an absorbent chassis support member which includes a strip of material which is directly attached to said laterally opposed side edges of said outer cover adjacent at least one of said fasteners and said unattached portion of said absorbent chassis and which extends between said absorbent chassis and said laterally opposed side edges of said outer cover wherein said absorbent chassis support member is configured to maintain said absorbent chassis close to a wearer's body in use.

27. The absorbent article of claim 26 wherein said outer cover is a nonwoven material.

28. The absorbent article of claim 26 wherein said absorbent article further comprises a pair of leg elastics which are respectively located on said pair of laterally opposed side edges of said outer cover in at least said crotch region of said outer cover.

29. The absorbent article of claim 26 wherein at least about 95 percent of said longitudinal length of said absorbent chassis is not directly attached to said outer cover.

30. The absorbent article of claim 26 wherein said absorbent article further comprises a pair of longitudinally extending containment flaps which are respectively located on a pair of laterally opposed side edges of said absorbent chassis.

31. The absorbent article of claim 24 wherein said absorbent chassis support member remains substantially unattached to said outer cover between said side edges of said outer cover.

32. The absorbent article of claim 31 wherein a portion of said absorbent chassis support member which remains unattached to said outer cover is attached to said backsheet of said absorbent chassis to maintain said absorbent chassis close to said wearer's body in use.

33. The absorbent article of claim 26 wherein said absorbent chassis support member is a strip of nonwoven material which defines a width of from about 2 to about 5 centimeters.

34. The absorbent article of claim 26 wherein said primary fasteners are configured to encircle a wearer's hips and engage an outer surface of said outer cover in said opposite waist region of said outer cover to maintain said absorbent article about said wearer in use.

35. The absorbent article of claim 34 wherein said primary fasteners are located in said back waist region of said outer cover and are configured to releasably engage said outer surface of said outer cover in said front waist region of said outer cover.

36. The absorbent article of claim 24 wherein said secondary fasteners are configured to engage a body facing surface of said absorbent chassis in use.

37. The absorbent article of claim 36 wherein said secondary fasteners are located in said front waist region of said outer cover and are configured to releasably engage said body facing surface of said absorbent chassis in said rear waist region of said outer cover.

* * * * *

UNITED STATES PATENT AND TRADEMARK OFFICE
CERTIFICATE OF CORRECTION

PATENT NO.    : 6,142,983
DATED         : November 7, 2000
INVENTOR(S)   : Jody Dorothy Suprise et al.

It is certified that error appears in the above-identified patent and that said Letters Patent is hereby corrected as shown below:

<u>Column 18,</u>
Line 9, delete "24", and substitute -- 26 --.
Line 33, delete "24", and substitute -- 26 --.

Signed and Sealed this

Thirteenth Day of August, 2002

*Attest:*

*Attesting Officer*

JAMES E. ROGAN
*Director of the United States Patent and Trademark Office*